United States Patent

Iwase et al.

Patent Number: 5,089,494
Date of Patent: Feb. 18, 1992

[54] 4-PHENYLPHTHALAZINE DERIVATIVES WHICH INHIBIT PLATELET AGGREGATION

[75] Inventors: Norimichi Iwase, Yokohama; Yasuhiro Morinaka, Tsuchiura; Yoshikuni Tamao, Machida; Toshiji Kanayama, Yokohama, all of Japan

[73] Assignee: Mitsubishi Kasei Corporation, Tokyo, Japan

[21] Appl. No.: 675,259

[22] Filed: Mar. 27, 1991

[30] Foreign Application Priority Data

Mar. 30, 1990 [JP] Japan .................. 2-85447

[51] Int. Cl.$^5$ ............ A61K 31/50; C07D 237/34; C07D 405/12; C07D 405/14
[52] U.S. Cl. .................... 514/248; 544/237
[58] Field of Search .............. 544/237, 248

[56] References Cited

FOREIGN PATENT DOCUMENTS 0159652 10/1985 European Pat. Off. .
2021195 11/1970 Fed. Rep. of Germany .
1303061 1/1973 United Kingdom .
2063249 6/1981 United Kingdom .

OTHER PUBLICATIONS

Patent Abstracts of Japan, vol. 5, No. 114 (C-64) (786) 23 Jul. 1981, of JP-A-56 53659 (Mitsubishi Yuki Yakuhin K.K.) 13 May 1981, [cat. D].
Patent Abstracts of Japan, vol. 5, No. 114 (-64) (786) 23 Jul. 1981, of JP-A-56 53660 (Mitsubishi Yuka Yakuhin K.K.) 13 May 1981, [cat. D].
Patent Abstracts of Japan, vol. 10, No. 112 (-342) (2169) 25 Apr. 1986, of JP-A-60 243074 (Mitsubishi Yuka Yakuhin K.K.) 03 December 1985, [cat. D].
Chemical Abstracts, vol. 71, (Aug. 1969) Columbus, Ohio, USA H. H. Holava, Jr., et al.: "1-Substituted 4-aryl-[or 4-aralkyl-]phthalazines", ref. No. 22093A. Holava, J Med. Chem. 12, 555 (1969).

Primary Examiner—Mark L. Berch
Attorney, Agent, or Firm—Wenderoth, Lind & Ponack

[57] ABSTRACT

4-Phenylphthalazine derivatives having platelet aggregation inhibitory activity of the formula:

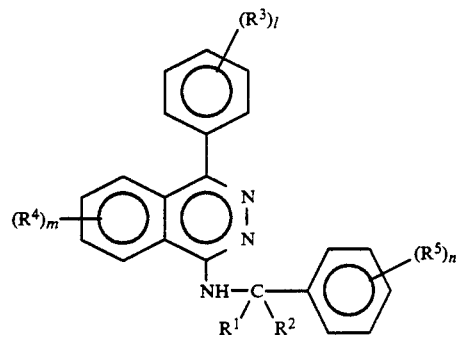

wherein $R^1$ is an alkyl or hydroxyalkyl group of 1–5 carbon atoms; $R^2$ is a hydrogen atom or an alkyl group of 1–5 carbon atoms; or $R^1$ and $R^2$, when taken together, may represent an alkylene group of 2–6 carbon atoms, said group optionally containing one or more oxygen atoms; $R^3$ and $R^4$ are independently a hydrogen or halogen atom, an alkyl or alkoxy group of 1–4 carbon atoms, or when two of $R^3$ are adjacently positioned, $(R^3)_l$ may represent a $-O-(CH_2)_p-O-$ group and/or when two of $R^4$ are adjacently positioned, $(R^4)_m$ may represent a $-O-(CH_2)_p-O-$ group; $R^5$ is a hydrogen or halogen atom, an alkyl or alkoxy group of 1–4 carbon atoms, a trifluoromethyl group or a hydroxy group, or when two of $R^5$ are adjacently positioned, $(R^5)_n$ may represent a $-O-(CH_2)_p-O-$ group; p is an integer of 1–3; l and m are independently an integer of 1–2; and n is an integer of 1–3, and optical isomers and pharmaceutically acceptable acid addition salts thereof.

13 Claims, No Drawings

4-PHENYLPHTHALAZINE DERIVATIVES WHICH INHIBIT PLATELET AGGREGATION

The present invention relates to aminophthalazine derivatives having platelet aggregation inhibitory activity and thus being useful as prophylactic or therapeutic agents for cerebrovascular diseases such as cerebral thrombosis, cerebral embolus or the like, ischemic heart diseases such as cardiac infarction or the like, and circulatory disorders such as peripheral circular disease. More particularly, this invention is directed to 1-α-substitutedbenzylamino-4-phenylphthalazine derivatives or their pharmaceutically acceptable acid addition salts.

Ischemic heart diseases such as cardiac infarction, angina pectoris or the like, cerebrovascular diseases such as cerebral thrombosis, cerebral embolus or the like and circulatory disorders such as peripheral circulatory disease are often attributable to generation of intravascular thrombosis which blocks the vessel. This phenomenon is mainly based on the platelet aggregation which takes place at the preliminary stage of thrombosis formation.

Many 4-phenylphthalazine derivatives have heretofore been known as having platelet aggregation-inhibitory activity. For example, Japanese Patent Publication (Kokai) Nos. 53659/1981, 53660/1981 and 4897/1982 disclose 1-anilino-4-phenylphthalazine derivatives, and Japanese Patent Publication (Kokai) Nos. 218377/1985 and 243074/1985 disclose that the following two compounds show potent platelet aggregation-inhibitory activity in vitro.

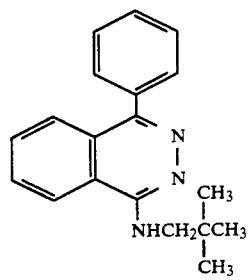

(II)

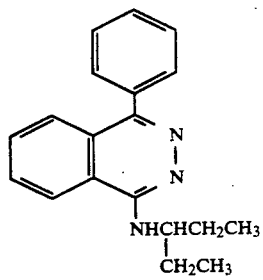

(III)

However, some of these known compounds hardly show the activity when orally administrated, and others have only insufficient platelet aggregation-inhibitory activity in vivo.

On the other hand, 1-amino-4-phenylphthalazine derivatives of the following formula (IV) are disclosed in British Patent No. 1,303,061, J. Med. Chem., 12, 555 (1969) and the like.

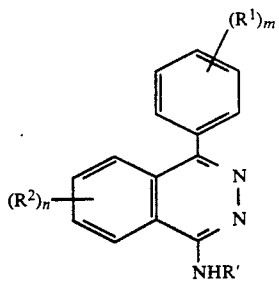

(IV)

However, only a few compounds are specifically disclosed in the above literatures, and as for the pharmacological activity, only antiinflammatory activity and antirheumatic activity are described therein.

As the result of investigations on the 4-phenylphthalazine derivatives to find out compounds having excellent platelet aggregation inhibitory activity in vivo and also having an activity directly inhibiting the undesirable affecting change in the affected region such as shrinkage of cardiac infarction nest or the like, the present inventors have discovered that the 4-phenylphthalazines having special α-substitutedbenzylamino group at the 1-position suffice the above requirements.

Accordingly, the present invention provides 4-phenylphthalazine derivatives of the following formula (I):

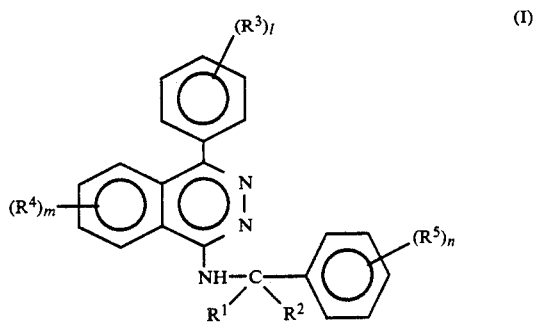

(I)

wherein $R^1$ is an alkyl or hydroxyalkyl group of 1–5 carbon atoms; $R^2$ is a hydrogen atom or an alkyl group of 1–5 carbon atoms; or $R^1$ and $R^2$, when taken together, may represent an alkylene group of 2–6 carbon atoms, said group optionally containing one or more oxygen atoms; $R^3$ and $R^4$ are independently a hydrogen or halogen atom, an alkyl or alkoxy group of 1–4 carbon atoms, or when two of $R^3$ are adjacently positioned, $(R^3)_l$ may represent a $-O-(CH_2)_p-O-$ group and/or when two of $R^4$ are adjacently positioned, $(R^4)_m$ may represent a $-O-(CH_2)_p-O-$ group; $R^5$ is a hydrogen or halogen atom, an alkyl or alkoxy group of 1–4 carbon atoms, a trifluoromethyl group or a hydroxy group, or when two of $R^5$ are adjacently positioned, $(R^5)_n$ may represent a $-O-(CH_2)_p-O-$ group; p is an integer of 1–3; l and m are independently an integer of 1–2; and n is an integer of 1–3, and optical isomers and pharmaceutically acceptable acid addition salts thereof. The present invention will be explained below in detail.

In the compounds of the present invention represented by the general formula (I), $R^1$ is an alkyl group of 1 to 5 carbon atoms such as methyl group, ethyl group, n-propyl group, i-propyl group, n-butyl group, i-butyl group, sec-butyl group, tert-butyl group, n-pentyl group, neopentyl group, or 1-ethylpropyl group or a hydroxyalkyl group of 1-5 carbon atoms such as hydroxymethyl group, 2-hydroxyethyl group, 1-hydroxyethyl group, 3-hydroxypropyl group, 1-methyl-2-hydroxyethyl group, 4-hydroxybutyl group, 1,1-dimethyl-2-hydroxyethyl group, 2-methyl-3-hydroxypropyl group, 5-hydroxylpentyl group, or 2,2-dimethyl-3-hydroxypropyl group. $R^2$ is a hydrogen atom or an alkyl group of 1-5 carbon atoms such as methyl group, ethyl group, n-propyl group, i-propyl group, n-butyl group, i-butyl group, sec-butyl group, tert-butyl group, n-pentyl group, neopentyl group, or 1-ethylpropyl group. However, $R^1$ and $R^2$ may combine together and represent an alkylene group of 2-6 carbon atoms optionally containing one or more oxygen atoms, such as ethylene group, trimethylene group, tetramethylene group, pentamethylene group, hexamethylene group, -$CH_2OCH_2$-group, -$CH_2CH_2OCH_2CH_2$- group, and the like. $R^3$ and $R^4$ are independently hydrogen atom; halogen atom such as fluorine atom, chlorine atom, bromine atom or the like; alkyl group of 1 to 4 carbon atoms such as methyl group, ethyl group, n-propyl group, i-propyl group, n-butyl group, tert-butyl group or the like; or alkoxy group of 1 to 4 carbon atoms such as methoxy group, ethoxy group, n-propoxy group, i-propoxy group, n-butoxy group, i-butoxy group or the like. $R^5$ is hydrogen atom; halogen atom such as fluorine atom, chlorine atom, bromine atom or the like; alkyl group of 1 to 4 carbon atoms such as methyl group, ethyl group, n-propyl group, i-propyl group, n-butyl group, i-butyl group, tert-butyl group or the like; or alkoxy group of 1 to 4 carbon atoms such as methoxy group, ethoxy group, n-propoxy group, i-propoxy group, n-butoxy group, i-butoxy group or the like; trifluoromethyl group or hydroxy group. However, two of $R^3$, $R^4$ or $R^5$, when adjacently positioned, may form methylenedioxy group, ethylenedioxy group or trimethylenedioxy group. Finally, l and m are independently an integer of 1 or 2, and n is an integer of 1 to 3.

Preferred compounds of the present invention are those of the formula (I) wherein:

(i) $R^1$ is an alkyl group of 1-5 carbon atoms or a hydroxyalkyl of 1-3 carbon atoms; $R^2$ is a hydrogen atom or an alkyl group of 1-5 carbon atoms; or $R^1$ and $R^3$, taken together, represent an alkylene group of 4-6 carbon atoms;

(ii) $R^3$ and $R^4$ are independently a hydrogen or halogen atom, or an alkyl or alkoxy group of 1-4 carbon atoms; and/or (iii) $R^5$ is a hydrogen or halogen atom, an alkyl or alkoxy group of 1-4 carbon atoms, or a trifluoromethyl group; or two of $R^5$ adjacently positioned represent -O-$(CH_2)_p$-O- group.

More preferred compounds (I) of the present invention are those wherein:

(iv) $R^1$ is an alkyl group of 1-5 carbon atoms, $R^2$ is a hydrogen atom or an alkyl group of 1-5 carbon atoms, or $R^1$ and $R^2$, taken together, represent an alkylene group of 4-6 carbon atoms;

(v) $R^3$ and $R^4$ are independently a hydrogen, fluorine, or chlorine atom, or an alkyl or alkoxy group of 1-3carbon atoms; and/or (vi) $R^5$ is a hydrogen or halogen atom, or an alkyl or alkoxyl group of 1-4 carbon atoms.

Most preferred compounds (I) are those in which l, m, and n are 1.

The following Table 1 shows illustrative examples of the compounds in the present invention, but their respective isomers as well as their mixture are included in the present invention.

TABLE 1

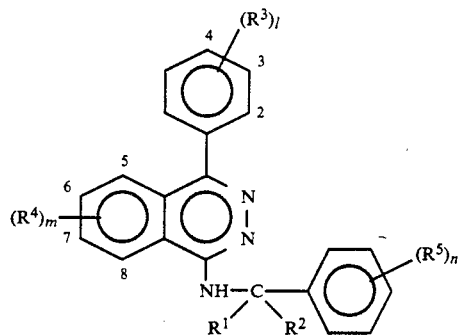

| Compound No. | $R^1$ | $R^2$ | $R^3$ | $R^4$ | $R^5$ |
|---|---|---|---|---|---|
| 1 | —$CH_3$ | H | H | H | H |
| 2 | —$CH_2CH_3$ | H | H | H | H |
| 3 | —$CH_2CH_2CH_3$ | H | H | H | H |
| 4 | —$CH(CH_3)_2$ | H | H | H | H |
| 5 | —$CH_2CH_2CH_2CH_3$ | H | H | H | H |
| 6 | —$CH_2CH(CH_3)CH_3$ | H | H | H | H |
| 7 | —$CH_2(CH_3)CH_2CH_3$ | H | H | H | H |
| 8 | -t-$C_4H_9$ | H | H | H | H |
| 9 | —$CH_2(CH_2)_3CH_3$ | H | H | H | H |
| 10 | —$CH_2C(CH_3)_3$ | H | H | H | H |
| 11 | —$CH(CH_2CH_3)_2$ | H | H | H | H |
| 12 | —$CH(CH_3)CH_2CH_2CH_3$ | H | H | H | H |
| 13 | —$CH_3$ | H | 4-$CH_3$ | H | H |
| 14 | —$CH_2CH_3$ | H | 4-$CH_3$ | H | H |
| 15 | -t-$C_4H_9$ | H | 4-$CH_3$ | H | H |
| 16 | —$CH_3$ | H | 4-$CH_2CH_3$ | H | H |
| 17 | —$CH_3$ | H | 4-$CH_2CH_2CH_3$ | H | H |
| 18 | —$CH_3$ | H | 4-$CH(CH_3)_2$ | H | H |
| 19 | —$CH_3$ | H | 4-$C_4H_9$ | H | H |
| 20 | —$CH_3$ | H | 3-$CH_3$ | H | H |

TABLE 1-continued

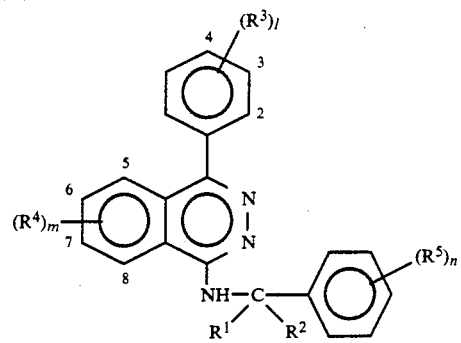

| Compound No. | $R^1$ | $R^2$ | $R^3$ | $R^4$ | $R^5$ |
|---|---|---|---|---|---|
| 21 | —CH$_3$ | H | 2-CH$_3$ | H | H |
| 22 | —CH$_3$ | H | 3,4-diCH$_3$ | H | H |
| 23 | —CH$_3$ | H | 4-OCH$_3$ | H | H |
| 24 | —CH$_2$CH$_3$ | H | 4-OCH$_3$ | H | H |
| 25 | -t-C$_4$H$_9$ | H | 4-OCH$_3$ | H | H |
| 26 | —CH$_3$ | H | 4-OCH$_2$CH$_3$ | H | H |
| 27 | —CH$_3$ | H | 4-OCH$_2$CH$_2$CH$_3$ | H | H |
| 28 | —CH$_3$ | H | 4-OCH(CH$_3$)$_2$ | H | H |
| 29 | —CH$_3$ | H | 4-OC$_4$H$_9$ | H | H |
| 30 | —CH$_3$ | H | 3-OCH$_3$ | H | H |
| 31 | —CH$_3$ | H | 2-OCH$_3$ | H | H |
| 32 | —CH$_3$ | H | 3,4-diOCH$_3$ | H | H |
| 33 | —CH$_3$ | H | 3,4-OCH$_2$O | H | H |
| 34 | —CH$_3$ | H | 4-Cl | H | H |
| 35 | —CH$_2$CH$_3$ | H | 4-Cl | H | H |
| 36 | -t-C$_4$H$_9$ | H | 4-Cl | H | H |
| 37 | —CH$_3$ | H | 3-Cl | H | H |
| 38 | —CH$_3$ | H | 2-Cl | H | H |
| 39 | —CH$_3$ | H | 3,4-diCl | H | H |
| 40 | —CH$_3$ | H | 4-F | H | H |
| 41 | —CH$_2$CH$_3$ | H | 4-F | H | H |
| 42 | -t-C$_4$H$_9$ | H | 4-F | H | H |
| 43 | —CH$_3$ | H | 4-Br | H | H |
| 44 | —CH$_3$ | H | H | 6,7-diCH$_3$ | H |
| 45 | —CH$_2$CH$_3$ | H | H | 6,7-diCH$_3$ | H |
| 46 | -t-C$_4$H$_9$ | H | H | 6,7-diCH$_3$ | H |
| 47 | —CH$_3$ | H | H | 6,7-diOCH$_3$ | H |
| 48 | —CH$_2$CH$_3$ | H | H | 6,7-diOCH$_3$ | H |
| 49 | -t-C$_4$H$_9$H | H | H | 6,7-diOCH$_3$ | H |
| 50 | —CH$_3$ | H | H | 6,7-OCH$_2$O | H |
| 51 | —CH$_2$CH$_3$ | H | H | 6,7-OCH$_2$O | H |
| 52 | -t-C$_4$H$_9$ | H | H | 6,7-OCH$_2$O | H |
| 53 | —CH$_3$ | H | H | 6,7-diCl | H |
| 54 | —CH$_2$CH$_3$ | H | H | 6,7-diCl | H |
| 55 | -t-C$_4$H$_9$ | H | H | 6,7-diCl | H |
| 56 | —CH$_3$ | H | H | H | 4-CH$_3$ |
| 57 | —CH$_3$ | H | H | H | 3-CH$_3$ |
| 58 | —CH$_3$ | H | H | H | 2-CH$_3$ |
| 59 | —CH$_3$ | H | H | H | 4-CH$_2$CH$_3$ |
| 60 | —CH$_3$ | H | H | H | 4-CH$_2$CH$_2$CH$_3$ |
| 61 | —CH$_3$ | H | H | H | 4-CH(CH$_3$)$_2$ |
| 62 | —CH$_3$ | H | H | H | 4-C$_4$H$_9$ |
| 63 | —CH$_3$ | H | H | H | 3,4-diCH$_3$ |
| 64 | —CH$_3$ | H | H | H | 3,5-diCH$_3$ |

TABLE 1-continued

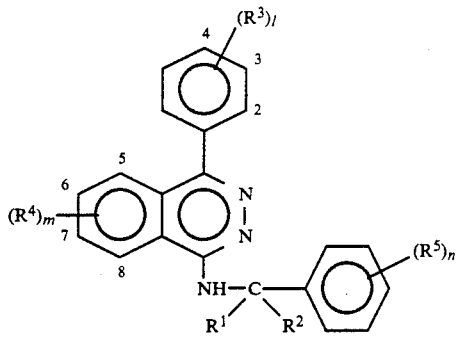

| Compound No. | R¹ | R² | R³ | R⁴ | R⁵ |
|---|---|---|---|---|---|
| 65 | —CH₃ | H | H | H | 2,4-diCH₃ |
| 66 | —CH₃ | H | H | H | 2,4,6-triCH₃ |
| 67 | —CH₂CH₃ | H | H | H | 4-CH₃ |
| 68 | -t-C₄H₉ | H | H | H | 4-CH₃ |
| 69 | —CH₃ | H | H | H | 4-OCH₃ |
| 70 | —CH₂CH₃ | H | H | H | 4-OCH₃ |
| 71 | -t-C₄H₉ | H | H | H | 4-OCH₃ |
| 72 | —CH₃ | H | H | H | 3-OCH₃ |
| 73 | —CH₃ | H | H | H | 2-OCH₃ |
| 74 | —CH₃ | H | H | H | 4-OCH₂CH₃ |
| 75 | —CH₃ | H | H | H | 4-OCH₂CH₂CH₃ |
| 76 | —CH₃ | H | H | H | 4-OCH(CH₃)₂ |
| 77 | —CH₃ | H | H | H | 4-OC₄H₉ |
| 78 | —CH₃ | H | H | H | 3,4-diOCH₃ |
| 79 | —CH₃ | H | H | H | 3,4-OCH₂O |
| 80 | —CH₃ | H | H | H | 4-Cl |
| 81 | —CH₃ | H | H | H | 3-Cl |
| 82 | —CH₃ | H | H | H | 2-Cl |
| 83 | —CH₂CH₃ | H | H | H | 4-Cl |
| 84 | -t-C₄H₉ | H | H | H | 4-Cl |
| 85 | —CH₃ | H | H | H | 4-F |
| 86 | —CH₃ | H | H | H | 3-F |
| 87 | —CH₃ | H | H | H | 2-F |
| 88 | —CH₂CH₃ | H | H | H | 4-F |
| 89 | -t-C₄H₉ | H | H | H | 4-F |
| 90 | —CH₃ | H | H | H | 4-Br |
| 91 | —CH₃ | H | H | H | 4-CF₃ |
| 92 | —CH₃ | H | H | H | 3-CF₃ |
| 93 | —CH₃ | H | H | H | 2-CF₃ |
| 94 | —CH₂CH₃ | H | H | H | 4-CF₃ |
| 95 | -t-C₄H₉ | H | H | H | 4-CF₃ |
| 96 | —CH₃ | H | H | H | 4-OH |
| 97 | —CH₃ | H | H | H | 3-OH |
| 98 | —CH₃ | H | H | H | 3,4-diOH |
| 99 | —CH₃ | H | H | H | 3-CH₃, 4-Cl |
| 100 | —CH₃ | H | 4-CH₃ | H | 4-CH₃ |
| 101 | —CH₂CH₃ | H | 4-CH₃ | H | 4-CH₃ |
| 102 | —CH₃ | H | 4-CH₃ | H | 3-CH₃ |
| 103 | —CH₃ | H | 4-CH₃ | H | 4-Cl |
| 104 | —CH₃ | H | 4-CH₃ | H | 3-Cl |
| 105 | —CH₂CH₃ | H | 4-CH₃ | H | 3-Cl |
| 106 | —CH₃ | H | 4-Cl | H | 4-CH₃ |
| 107 | —CH₂CH₃ | H | 4-Cl | H | 4-CH₃ |
| 108 | —CH₃ | H | 4-Cl | H | 3-CH₃ |
| 109 | —CH₃ | H | 4-Cl | H | 4-Cl |
| 110 | —CH₃ | H | 4-F | H | 4-CH₃ |
| 111 | —CH₂CH₃ | H | 4-F | H | 4-CH₃ |
| 112 | —CH₃ | H | H | 6,7-diCH₃ | 4-CH₃ |
| 113 | —CH₃ | H | H | 6,7-diCH₃ | 3-CH₃ |
| 114 | —CH₃ | H | H | 6,7-diCH₃ | 4-Cl |
| 115 | —CH₂CH₃ | H | H | 6,7-diCH₃ | 3-Cl |
| 116 | —CH₃ | H | 4-Cl | 6,7-diCH₃ | 4-CH₃ |
| 117 | —CH₃ | H | 4-Cl | 6,7-diCH₃ | 3-Cl |
| 118 | —CH₂OH | H | H | H | H |
| 119 | —CH₃ | —CH₃ | H | H | H |
| 120 | —CH₂CH₃ | —CH₃ | H | H | H |
| 121 | —CH₂CH₃ | —CH₂CH₃ | H | H | H |
| 122 | —CH₂CH₂CH₃ | —CH₃ | H | H | H |

TABLE 1-continued

[Structure: phthalazine with 1-phenyl (positions 2,3,4 with $(R^3)_l$), fused benzene at positions 5,6,7,8 with $(R^4)_m$, N-N ring, and NH-C(R^1)(R^2)-phenyl with $(R^5)_n$]

| Compound No. | R¹ | R² | R³ | R⁴ | R⁵ |
|---|---|---|---|---|---|
| 123 | —CH₂CH₂CH₃ | —CH₂CH₃ | H | H | H |
| 124 | —CH₂CH₂CH₃ | —CH₂CH₂CH₃ | H | H | H |
| 125 | —CH₂CH₂CH₂CH₃ | —CH₃ | H | H | H |
| 126 | —CH₂CH₂CH₂CH₃ | —CH₂CH₃ | H | H | H |
| 127 | —CH₂CH₂CH₂CH₃ | —CH₂CH₂CH₃ | H | H | H |
| 128 | —CH₂CH₂CH₂CH₃ | —CH₂CH₂CH₂CH₃ | H | H | H |
| 129 | —CH(CH₃)₂ | —CH₃ | H | H | H |
| 130 | —CH(CH₃)₂ | —CH₂CH₃ | H | H | H |
| 131 | -t-C₄H₉ | —CH₃ | H | H | H |
| 132 | -t-C₄H₉ | —CH₂CH₃ | H | H | H |
| 133 | —CH₂—C(CH₃)₃ | —CH₃ | H | H | H |
| 134 | —CH₂—C(CH₃)₃ | —CH₂CH₃ | H | H | H |
| 135 | —(CH₂)₄— | | H | H | H |
| 136 | —(CH₂)₅— | | H | H | H |
| 137 | —(CH₂)₆— | | H | H | H |
| 138 | —CH₂CH₂OCH₂CH₂— | | H | H | H |
| 139 | —CH₃ | —CH₃ | 4-CH₃ | H | H |
| 140 | —CH₂CH₃ | —CH₂CH₃ | 4-CH₃ | H | H |
| 141 | —(CH₂)₅— | | 4-CH₃ | H | H |
| 142 | —CH₃ | —CH₃ | 4-CH₂CH₃ | H | H |
| 143 | —CH₃ | —CH₃ | 4-CH₂CH₂CH₃ | H | H |
| 144 | —CH₃ | —CH₃ | 4-CH(CH₃)₂ | H | H |
| 145 | —CH₃ | —CH₃ | 3-CH₃ | H | H |
| 146 | —CH₃ | —CH₃ | 2-CH₃ | H | H |
| 147 | —CH₃ | —CH₃ | 4-OCH₃ | H | H |
| 148 | —CH₂CH₃ | —CH₂CH₃ | 4-OCH₃ | H | H |
| 149 | —(CH₂)₅— | | 4-OCH₃ | H | H |
| 150 | —CH₃ | —CH₃ | 4-OCH₂CH₃ | H | H |
| 151 | —CH₃ | —CH₃ | 4-OCH₂CH₂CH₃ | H | H |
| 152 | —CH₃ | —CH₃ | 4-OCH(CH₃)₂ | H | H |
| 153 | —CH₃ | —CH₃ | 3-OCH₃ | H | H |
| 154 | —CH₃ | —CH₃ | 2-OCH₃ | H | H |
| 155 | —CH₃ | —CH₃ | 4-Cl | H | H |
| 156 | —CH₂CH₃ | —CH₂CH₃ | 4-Cl | H | H |
| 157 | —(CH₂)₅— | | 4-Cl | H | H |
| 158 | —CH₃ | —CH₃ | 3-Cl | H | H |
| 159 | —CH₃ | —CH₃ | 2-Cl | H | H |
| 160 | —CH₃ | —CH₃ | 4-F | H | H |
| 161 | —CH₃ | —CH₃ | 4-Br | H | H |
| 162 | —CH₃ | —CH₃ | H | 6,7-diCH₃ | H |
| 163 | —CH₃ | —CH₃ | H | 6,7-diOCH₃ | H |

TABLE 1-continued

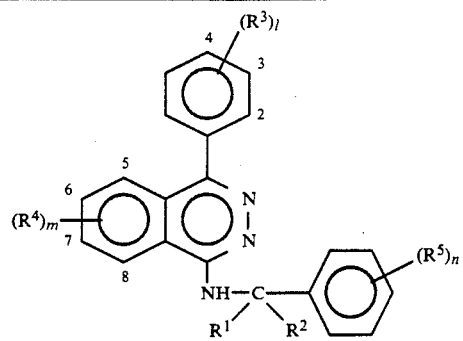

| Compound No. | $R^1$ | $R^2$ | $R^3$ | $R^4$ | $R^5$ |
|---|---|---|---|---|---|
| 164 | —CH₃ | —CH₃ | H | 6,7-O-CH₂-O | H |
| 165 | —CH₃ | —CH₃ | H | 6,7-diCl | H |
| 166 | —CH₃ | —CH₃ | H | H | 4-CH₃ |
| 167 | —CH₃ | —CH₃ | H | H | 3-CH₃ |
| 168 | —CH₃ | —CH₃ | H | H | 2-CH₃ |
| 169 | —CH₃ | —CH₃ | H | H | 4-CH₂CH₃ |
| 170 | —CH₃ | —CH₃ | H | H | 4-CH₂CH₂CH₃ |
| 171 | —CH₃ | —CH₃ | H | H | 4-CH(CH₃)₂ |
| 172 | —CH₃ | —CH₃ | H | H | 4-OCH₃ |
| 173 | —CH₃ | —CH₃ | H | H | 3-OCH₃ |
| 174 | —CH₃ | —CH₃ | H | H | 2-OCH₃ |
| 175 | —CH₃ | —CH₃ | H | H | 4-OCH₂CH₃ |
| 176 | —CH₃ | —CH₃ | H | H | 4-OCH₂CH₂CH₃ |
| 177 | —CH₃ | —CH₃ | H | H | 4-OCH(CH₃)₂ |
| 178 | —CH₃ | —CH₃ | H | H | 3,4-diOCH₃ |
| 179 | —CH₃ | —CH₃ | H | H | 3,4-O-CH₂-O |
| 180 | —CH₃ | —CH₃ | H | H | 4-Cl |
| 181 | —CH₃ | —CH₃ | H | H | 3-Cl |
| 182 | —CH₃ | —CH₃ | H | H | 2-Cl |
| 183 | —CH₃ | —CH₃ | H | H | 4-F |
| 184 | —CH₃ | —CH₃ | H | H | 3-F |
| 185 | —CH₃ | —CH₃ | H | H | 2-F |
| 186 | —CH₃ | —CH₃ | H | H | 4-CF₃ |
| 187 | —CH₃ | —CH₃ | H | H | 3-CF₃ |
| 188 | —CH₃ | —CH₃ | H | H | 2-CF₃ |
| 189 | —CH₃ | —CH₃ | H | H | 4-OH |
| 190 | —CH₃ | —CH₃ | H | H | 3-OH |
| 191 | —CH₃ | —CH₃ | H | H | 2-OH |

Note:
Position numbers of substituents are given for showing the position of the substituents on relevant benzene ring, and are not necessarily consistent with the formal position number of the compound.

Production of the compounds of the present invention will be explained below. The compounds of the present invention can be prepared by any one of conventional methods. For example, the following synthetic process is illustrated.

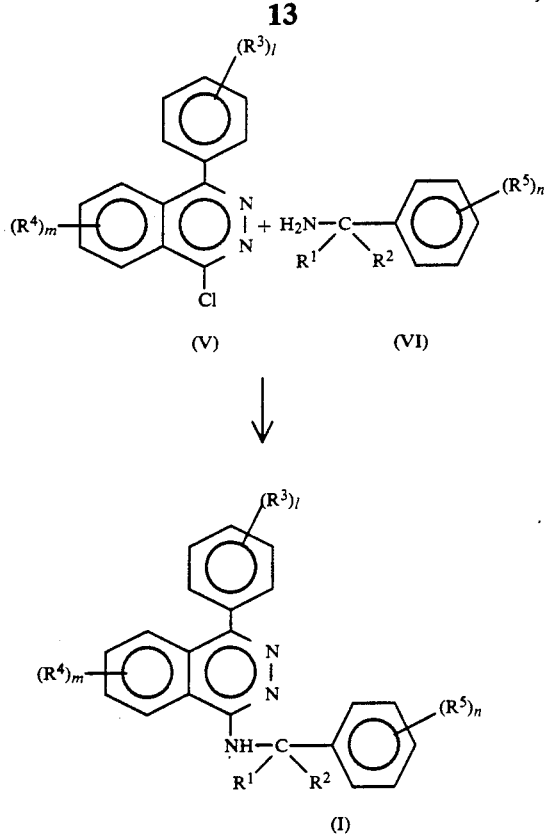

(wherein $R^1$, $R^2$, $R^3$, $R^4$, $R^5$, $l$, m and n have the same significance as defined above)

The above process consists of reacting the starting material (V) with the compound (VI) in the presence or absence of a base catalyst with or without a solvent.

The starting material (V) can be synthesized according to the process as described in Yakugaku Zasshi, 86 576 (1966).

The reaction is generally carried out at temperature from 0° to 250° C., preferably from 20° to 200° C. over a period of 10 minutes to 24 hours. Examples of the solvents, when used, are ethers such as tetrahydrofuran, dioxane or the like, halogenohydrocarbons such as chloroform, methylene chloride or the like, aromatic hydrocarbons such as benzene, toluene, xylene, chlorobenzene or the like, amides such as dimethylformamide, dimethylacetamide, N-methylpyrrolidone or the like, or dimethyl sulfoxide. The amount of the solvent may range from 0.1 to 100 parts by weight with respect to the compound (V). Examples of the catalysts, when used, are organic bases such as triethylamine, diisopropylamine, N,N-dimethylaniline, pyridine or the like or inorganic bases such as sodium hydride, sodium hydrogen carbonate, sodium carbonate, potassium carbonate, sodium hydroxide, potassium hydroxide or the like. The amount of the catalyst to be used may range between 0.5 and 5 mol, preferably 1 and 3 mol with respect to the compound (V). Appropriate amount of the compound (VI) to be used in the reaction is generally 0.5 to 30 mol, preferably 1 to 10 mol, with respect to the compound (V).

After completion of the reaction, and after removal of the solvent if necessary, the reaction mixture may be poured into an excessive amount of water or dissolved in a solvent such as dichloromethane or the like. Then it may be neutralized with an aqueous alkali solution and the product may be purified in a conventional manner such as recrystallization or chromatography.

Physiologically acceptable salts of the compounds (I) are preferable as their salts. For example, there are exemplified an inorganic acid salt such as hydrochloride, hydroiodide, sulfate, phosphate or the like, and an organic acid salt such as methanesulfonate, p-toluenesulfonate, benzenesulfonate, camphor sulfonate, acetate, benzoate, malate, lactate, glycolate, glucuronate, maleate, fumarate, succinate, ascorbate, citrate, salicylate, nicotinate, tartarate or the like. Since the compounds (I) and their salts may exists in the form of hydrate or solvated product, these hydrate and solvated product may be included in the compounds of the present invention.

When the compound of the present invention is applied clinically as a circulatory improving agent, appropriate single dosage for adult is 1 to 100 mg for oral administration, and it is given 1 to 3 times per day. For intravenous administration, 0.01 to 10 mg is an appropriate single dosage and it is given 2 to 5 times per day for adult. For rectal administration, 1 to 100 mg is preferred single dosage and it is applied 1 to 3 times per day for adult. Preferably, said dosage may be appropriately increased or reduced, depending upon age, pathology and symptoms of particular patient.

Pharmaceutical formulation can be prepared by admixing at least one of the compounds (I) or pharmaceutically acceptable salts thereof with customarily usable pharmaceutical carriers, lubricants and other additives. The carrier may be solid or liquid. The solid carrier illustratively includes lactose, kaolin, sucrose, crystalline cellulose, corn starch, talc, agar, pectin, acasia, stearic acid, magnesium stearate, lecithin, sodium chloride and the like.

The liquid carrier illustratively includes syrup, glycerin, peanut oil, polyvinylpyrrolidone, olive oil, ethanol, benzyl alcohol, propylene glycol, water and the like.

The pharmaceutical formulation may take various types. When the solid carrier is used, tablets, powders, granules, hard gelatin capsules, suppositories, or troches may be formulated. Appropriate amount of the solid carrier may vary broadly, but it is preferably about 1 mg to about 1 g per single dosage.

Syrups, emulsions, soft gelatin capsules, sterilized injections, or aqueous or non-aqueous suspensions may be prepared using liquid carrier.

The following detailed examples are presented by way of illustration of certain specific embodiments of the invention.

EXAMPLE 1

Preparation of
D-1-α-methylbenzylamino-4-phenylphthalazine
(D-form of Compound No. 1 in Table 1)

To 5 ml of N-methylpyrrolidone were added 5.0 g of 1-chloro-4-phenylphthalazine (Compound V) and 5.0 g of D-α-methylbenzylamine, and the resultant mixture was stirred with heating at 130° to 140° C. for 3 hours. After finishing the reaction, the mixture was cooled, mixed with 20 ml of 5% aqueous sodium hydroxide and extracted with chloroform. The organic layer was separated and dried over magnesium sulfate, concentrated and purified on a silica gel column (eluent: ethyl acetate-n-hexane-chloroform). The product was recrystallized from ethyl acetate-n-hexane to give 3.31 g of D-1-

α-methylbenzylamino-4-phenylphthalazine as colorless crystals. M.P. 184° to 185.5° C.

EXAMPLE 2 to 38

The compounds listed in the following Table 2 were prepared in the same manner as in Example 1.

with chloroform with addition of 5% NaOH aqueous solution. The organic layer was separated, dried over $MgSO_4$, concentrated, and purified by silica gel chromatography. The resultant product was recrystallized using chloroform and ether to obtain 1-α,α-dimethylbenzylamino-4-phenylphthalazine as colorless crystals.

TABLE 2

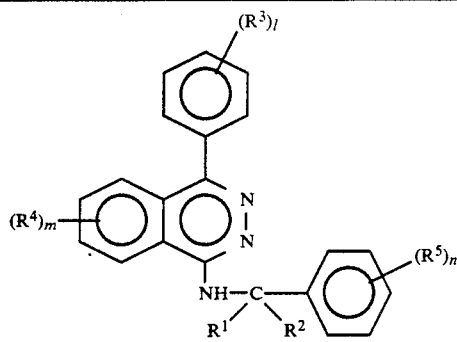

| Example | Compound No. | $R_1$ | $R_2$ | $R_3$ | $R_4$ | $R_5$ | M.P. (°C.) |
|---|---|---|---|---|---|---|---|
| 2 | 1 (L) | —CH₃ | H | H | H | H | 185 to 186.5 |
| 3 | 1 (DL) | —CH₃ | H | H | H | H | 196.5 to 197.5 |
| 4 | 2 (DL) | —CH₂CH₃ | H | H | H | H | 164.5 to 165 |
| 5 | 4 (DL) | —CH(CH₃)₂ | H | H | H | H | 188 to 189 |
| 6 | 5 (DL) | -n-C₄H₉ | H | H | H | H | 129 to 131 |
| 7 | 8 (DL) | -t-C₄H₉ | H | H | H | H | 237 to 237.5 |
| 8 | 34 (DL) | —CH₃ | H | 4-Cl | H | H | 213.5 to 214 |
| 9 | 81 (DL) | —CH₃ | H | H | H | 3-Cl | 184 to 184.5 |
| 10 | 3 (DL) | —CH₂CH₂CH₃ | H | H | H | H | 154 to 155 |
| 11 | 13 (D) | —CH₃ | H | 4-CH₃ | H | H | 136 to 139 |
| 12 | 20 (D) | —CH₃ | H | 3-CH₃ | H | H | 132 to 135 |
| 13 | 21 (D) | —CH₃ | H | 2-CH₃ | H | H | 182 to 183 |
| 14 | 23 (D) | —CH₃ | H | 4-OCH₃ | H | H | 195 to 197 |
| 15 | 30 (D) | —CH₃ | H | 3-OCH₃ | H | H | 155 to 156 |
| 16 | 31 (D) | —CH₃ | H | 2-OCH₃ | H | H | 123 to 126 |
| 17 | 37 (D) | —CH₃ | H | 3-Cl | H | H | 165 to 172 |
| 18 | 40 (D) | —CH₃ | H | 4-F | H | H | 180.5 to 181.5 |
| 19 | 44 (D) | —CH₃ | H | H | 6,7-diCH₃ | H | 176 to 179 |
| 20 | 53 (D) | —CH₃ | H | H | 6,7-diCl | H | 233 to 236 |
| 21 | 56 (DL) | —CH₃ | H | H | H | 4-CH₃ | 190.5 to 191.5 |
| 22 | 57 (DL) | —CH₃ | H | H | H | 3-CH₃ | 150 to 151.5 |
| 23 | 58 (DL) | —CH₃ | H | H | H | 2-CH₃ | 214 to 215 |
| 24 | 59 (DL) | —CH₃ | H | H | H | 4-CH₂CH₃ | 156 to 159 |
| 25 | 69 (DL) | —CH₃ | H | H | H | 4-OCH₃ | 156.5 to 158 |
| 26 | 72 (DL) | —CH₃ | H | H | H | 3-OCH₃ | 197 to 198 |
| 27 | 73 (DL) | —CH₃ | H | H | H | 2-OCH₃ | 181 to 182.5 |
| 28 | 78 (DL) | —CH₃ | H | H | H | 3,4-diOCH₃ | 184 to 185 |
| 29 | 79 (DL) | —CH₃ | H | H | H | 3,4-O-CH₂-O | 135 to 137 |
| 30 | 80 (DL) | —CH₃ | H | H | H | 4-Cl | 145 to 146.5 |
| 31 | 82 (DL) | —CH₃ | H | H | H | 2-Cl | 241 to 245 |
| 32 | 85 (DL) | —CH₃ | H | H | H | 4-F | 152 to 152.5 |
| 33 | 86 (DL) | —CH₃ | H | H | H | 3-F | 180 to 183 |
| 34 | 87 (DL) | —CH₃ | H | H | H | 2-F | 227 to 229 |
| 35 | 91 (DL) | —CH₃ | H | H | H | 4-CF₃ | 215 to 217 |
| 36 | 92 (DL) | —CH₃ | H | H | H | 3-CF₃ | 180 to 181 |
| 37 | 118 (D) | —CH₂OH | H | H | H | H | 209 to 210 |
| 38 | 118 (L) | —CH₂OH | H | H | H | H | 207 to 210 |

EXAMPLE 39

Preparation of
1-α,α-dimethylbenzylamino-4-phenylphthalazine
(Compound No. 119 in Table 1)

To 4 ml of N-methylpyrrolidone were added 1.5 g of 1-chloro-4-phenylphthalazine and 2.1 g of α,α-dimethylbenzylamine, and the mixture was heated at 160° C. for 6 hours with stirring. After completion of the reaction, the reaction mixture was cooled, and extracted

M.P. 234°-235° C.

EXAMPLES 40-42

The compounds listed in the following Table 3 were prepared in the same manner as in Example 39.

TABLE 3

| Example | Compound No. | R₁ | R₂ | R₃ | R₄ | R₅ | M.P. (°C.) |
|---------|--------------|----|----|----|----|----|------------|
| 40 | 136 | —(CH₂)₅— | | H | H | H | 219 to 221 |
| 41 | 166 | —CH₃ | —CH₃ | H | H | 4-CH₃ | 221 to 224 |
| 42 | 167 | —CH₃ | —CH₃ | H | H | 3-CH₃ | 201 to 203 |

Experiment 1

Platelet aggregation-inhibitory activity in vitro

Rat arterial blood was centrifuged to obtain platelet rich plasma. To 250 µl of said platelet rich plasma was added 5 µl of a solution of the test compound, and the mixture was incubated for 2 minutes, mixed with 3 µl of collagen (Hormon-Chemie) as a platelet aggregation-inducer, and the change of platelet aggregation was observed and recorded for 10 minutes with 2 channels aggregometer (Sienco DP 247E).

Platelet aggregation inhibitory ratio was calculated by the following formula:

$$\text{Inhibitory ratio} = \frac{Tc - Ts}{Tc} \times 100$$

Tc: Aggregation degree where only a solvent was added.
Ts: Aggregation degree where a solution of the test compound was added.

Table 4 shows the inhibitory ratio of the compounds tested at each of the mol concentrations indicated.

Experiment 2

Platelet aggregation inhibitory activity ex vivo (by oral administration)

A group of 8 male Wistar ST rats each weighing about 250 grams were used. To the test animal was orally administered 4 ml/kg of a solution made by suspending a test compound in 1% aqueous tragacanth solution, and one hour later blood was collected from common carotid artery with a cannula. The blood was put in a plastic test tube in which 3.8% aqueous sodium citrate (1/10 volume) had been charged, and the mixture was stirred by overturning the tube, centrifuged by 200×g for 15 minutes, and the supernatant was recovered as platelet rich plasma (PRP). The residue was further centrifuged by 200033 g for 15 minutes and the supernatant was recovered as poor platelet plasma (PPP). The plasma samples were used for assaying the platelet aggregating ability. For assaying platelet aggregating ability, 2 channels aggregometer (Sienco DP 247E) was used, and the data were recorded on two pens recorder.

As an aggregation inducer, 7 to 10 µg/ml of collagen (Hormon-Chemie) was used.

Platelet Aggregation-inhibitory ratio was calculated by the following formula:

$$\text{Inhibitory ratio} = \frac{A - B}{A} \times 100 \, (\%)$$

A: Aggregating ratio of the group (control) in which only 1% aqueous tragacanth solution was administered.
B: Aggregating ratio of the group in which a solution of the test compound in tragacanth solution was administered.

Table 4 shows the test results.

TABLE 4

[Structure: a quinazoline-type core with (R³)ₗ on one phenyl, (R⁴)ₘ on fused ring, and NH—C(R¹)(R²)—phenyl(R⁵)ₙ substituent]

| Example No. | Compound No. in Table 1 | R¹ | R² | (R³)ₗ | (R⁴)ₘ | (R⁵)ₙ | in vitro Inhibitory ratio (%) $10^{-7}$ M | $3 \times 10^{-7}$ M | $10^{-6}$ M | ex vivo Inhibitory ratio (%) (p.o.) 10 mg/kg | 3 mg/kg | 1 mg/kg |
|---|---|---|---|---|---|---|---|---|---|---|---|---|
| 1 | 1 (D) | —CH₃ | —H | —H | —H | —H | 100 | | 100 | 88.5 | 80.2 | 65.5 |
| 3 | 1 (DL) | —CH₃ | —H | —H | —H | —H | 72.2 | | 84.0 | | 79.8 | 76.2 |
| 4 | 2 (DL) | —C₂H₅ | —H | —H | —H | —H | 100 | | 96.4 | 94.5 | 52.3 | 37.8 |
| 5 | 4 (DL) | —CH(CH₃)₂ | —H | —H | —H | —H | 49.3 | | 96.6 | | | |
| 6 | 5 (DL) | —C₄H₉ | —H | —H | —H | —H | 20.6 | | 98.4 | | | |
| 7 | 8 (DL) | —C₄H₉(t) | —H | —H | —H | —H | 100 | | 100 | 69.9 | 35.1 | 22.0 |
| 8 | 34 (DL) | —CH₃ | —H | 4-Cl | —H | —H | 100 | | 100 | | | |
| 9 | 81 (DL) | —CH₃ | —H | —H | —H | 3-Cl | 40.7 | 96.8 | 98.3 | 72.5 | | |
| 10 | 3 (D) | —C₃H₇ | —H | —H | —H | —H | 65.9 | 88.2 | | | | |
| 11 | 13 (D) | —CH₃ | —H | 4-CH₃ | —H | —H | 48.0 | | 94.3 | | | |
| 12 | 20 (D) | —CH₃ | —H | 3-CH₃ | —H | —H | 95.1 | | 76.8 | | | |
| 13 | 21 (D) | —CH₃ | —H | 2-CH₃ | —H | —H | 16.7 | | 92.9 | | | |
| 14 | 23 (D) | —CH₃ | —H | 4-OCH₃ | —H | —H | 4.8 | | 93.0 | | | |
| 15 | 30 (D) | —CH₃ | —H | 3-OCH₃ | —H | —H | | | | | | |
| 16 | 31 (D) | —CH₃ | —H | 2-OCH₃ | —H | —H | | | | | | |
| 17 | 37 (D) | —CH₃ | —H | 3-Cl | —H | —H | 91.9 | 93.4 | | | | |
| 18 | 40 (D) | —CH₃ | —H | 4-F | —H | —H | 14.2 | 66.3 | | | | |
| 19 | 44 (D) | —CH₃ | —H | —H | 6,7-diCH₃ | —H | 20.0 | 6.9 | | | | |
| 20 | 53 (D) | —CH₃ | —H | —H | 6,7-diCl | —H | | | 52.5 | | | |
| 21 | 56 (DL) | —CH₃ | —H | —H | —H | 4-CH₃ | 92.9 | | | | | |
| 22 | 57 (DL) | —CH₃ | —H | —H | —H | 3-CH₃ | 90.3 | | | | | |
| 23 | 58 (DL) | —CH₃ | —H | —H | —H | 2-CH₃ | 89.9 | | | | | |
| 24 | 59 (DL) | —CH₃ | —H | —H | —H | 4-C₂H₅ | 56.5 | | | | | 61.8 |
| 25 | 69 (DL) | —CH₃ | —H | —H | —H | 4-OCH₃ | 21.0 | 74.7 | | | | |
| 26 | 72 (DL) | —CH₃ | —H | —H | —H | 3-OCH₃ | 14.9 | | 94.8 | | | |
| 27 | 73 (DL) | —CH₃ | —H | —H | —H | 2-OCH₃ | 93.3 | | | | | |
| 28 | 78 (DL) | —CH₃ | —H | —H | —H | 3,4-diOCH₃ | 6.2 | 93.6 | | | | |
| 29 | 79 (DL) | —CH₃ | —H | —H | —H | 3,4-OCH₂O | 6.3 | 95.3 | | | | |

TABLE 4-continued
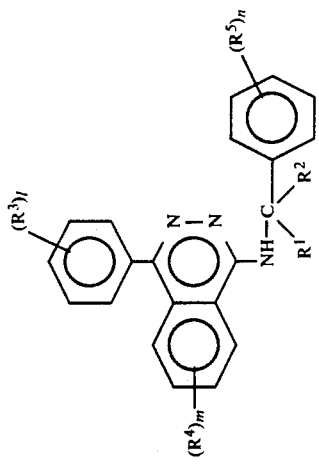
| Example No. | Compound No. in Table 1 | R¹ | R² | (R³)ₗ | (R⁴)ₘ | (R⁵)ₙ | in vitro Inhibitory ratio (%) | | | ex vivo Inhibitory ratio (%) (p.o.) | | |
|---|---|---|---|---|---|---|---|---|---|---|---|---|
| | | | | | | | $10^{-7}$ M | $3 \times 10^{-7}$ M | $10^{-6}$ M | 10 mg/kg | 3 mg/kg | 1 mg/kg |
| 30 | 80 (DL) | —CH₃ | —H | —H | —H | 4-Cl | 26.3 | 93.3 | | | | |
| 31 | 82 (DL) | —CH₃ | —H | —H | —H | 2-Cl | 10.2 | 58.5 | 65.5 | | | |
| 32 | 85 (DL) | —CH₃ | —H | —H | —H | 4-F | 100 | 94.1 | | | | |
| 33 | 86 (DL) | —CH₃ | —H | —H | —H | 3-F | | | 100 | | | |
| 34 | 87 (DL) | —CH₃ | —H | —H | —H | 2-F | | | 52.4 | | | |
| 35 | 91 (DL) | —CH₃ | —H | —H | —H | 4-CF₃ | 1.5 | | 22.5 | | | |
| 36 | 92 (DL) | —CH₃ | —H | —H | —H | 3-CF₃ | | | 89.5 | | | |
| 37 | 118 (D) | —CH₂OH | —H | —H | —H | —H | 30.2 | 6.0 | 49.1 | | | |
| 38 | 118 (L) | —CH₂OH | —H | —H | —H | —H | 93.0 | 94.4 | | | | |
| 39 | 119 | —CH₃ | —CH₃ | —H | —H | —H | 94.7 | | | | | |
| 40 | 136 | —(CH₂)₅— | | —H | —H | —H | 100 | | 100 | | | 40.5 |
| 41 | 166 | —CH₃ | —CH₃ | —H | —H | 4-CH₃ | 100 | | 100 | | | |
| 42 | 167 | —CH₃ | —CH₃ | —H | —H | 3-CH₃ | | | | | | |
| Control 1 | | | | | | | 11.0 | | 52.1 | 13.5 | | |
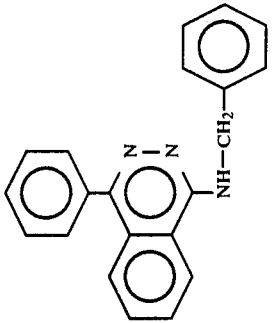

TABLE 4-continued
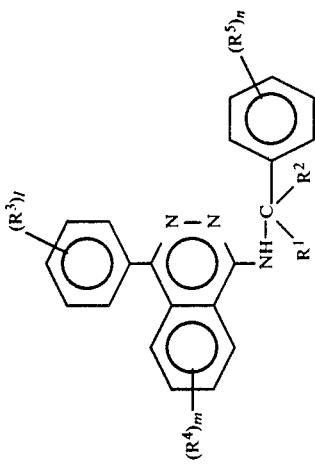
| Example No. | Compound No. in Table 1 | R¹ | R² | (R³)_l | (R⁴)_m | (R⁵)_n | in vitro Inhibitory ratio (%) | | | ex vivo Inhibitory ratio (%) (p.o.) | | |
|---|---|---|---|---|---|---|---|---|---|---|---|---|
| | | | | | | | $10^{-7}$ M | $3 \times 10^{-7}$ M | $10^{-6}$ M | 10 mg/kg | 3 mg/kg | 1 mg/kg |
| Control 2 | | | | | | | | | 0 | | | |
| Control 3 | | | | | | | 12.6 | | 40.7 | | | |

TABLE 4-continued
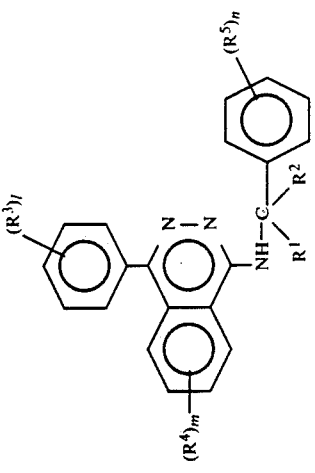
| Example No. | Compound No. in Table 1 | R¹ | R² | (R³)$_l$ | (R⁴)$_m$ | (R⁵)$_n$ | in vitro Inhibitory ratio (%) | | | ex vivo Inhibitory ratio (%) (p.o.) | | |
|---|---|---|---|---|---|---|---|---|---|---|---|---|
| | | | | | | | $10^{-7}$ M | $3 \times 10^{-7}$ M | $10^{-6}$ M | 10 mg/kg | 3 mg/kg | 1 mg/kg |
| Control 4 | | | | | | | | | 7.1 | | | |

Experiment 3

Activity of the compounds (I) to rat left coronary artery ligation-induced cardiac infarction A group of 8 male SD rats weighing 200 to 250 g were used. The rats were fixed at the dosal position under light ether paralysis, subjected to longitudinal incission in about 1.5 cm along the sternal left line to make thoractonomy under breaking the heart sac and exposing the heart. After ligating the left main coronary artery at 1 to 2 mm from the origin with black blade silk suture (Hama Ika Kogyo, 4-0), the heart was returned at the original position and the breast was closed immediately. The bilateral breast was pressed to exclude the air in the thoracic cavity to resume respiration. Electrocardiography (Nippon Koden, ECG-6601) showed ST elevation of II induction. Twenty-four hours after ligation, the blood was collected from the ventral vena cava, and the rat was killed by complete bleeding. The heart was taken out, and the cross circular slice (about 2 mm) at the central part of the heart was incubated at 37° C. in the dark for 20 minutes in 20 ml of 1% solution of TTC (tryphenyl tetrazolium chloride, Wako Junyaku) in 0.09 M phosphate buffer (pH 8.6). The slice was photographed under a stereoscopic microscope, and the colored slides were prepared therefrom. The slides were projected on the wall, and the sections, the infarction parts (TTC non-dyed part) and non-infarction parts (TTC dyed part), were traced. So, the area of the infarction part in the total section area was calculated. A solution made by suspending the test compound in 1% aqueous tragacanth solution was orally administered 60 minutes prior to the coronary artery ligation.

$$\text{Cardiac infarction inhibitory ratio} = \frac{A - B}{A} \times 100 \ (\%)$$

A: Infarction ratio where only 1% tragacanth solution was administered for control.
B: Infarction ratio where the tragacanth solution containing the test compound was administered.
Table 5 shows the test results.

TABLE 5

| Compound No. in Table 1 | Cardiac infarction inhibitory ratio | |
|---|---|---|
| | Dosage (mg/kg) | % |
| 1 (D) | 2 | 81.1 |
| 1 (D) | 10 | 76.6 |
| Aspirin* | 100 | 10.7 |
| Ticlopidine* | 30 | 10.1 |

*Commercially available platelet aggregation inhibitor

Since the compounds of the present invention inhibit remarkably platelet aggregation not only in vitro but in vivo by oral administration, these compounds are useful as a prophylactic or therapeutic agent for various circulatory disorders.

Further, these compounds can reduce the cardiac infarction nest by direct action without being based on platelet aggregation inhibitory activity. Accordingly, the compounds are highly useful for treating ischemic heart diseases.

What is claimed is:
1. 4-Phenylphthalazine compound of the formula:

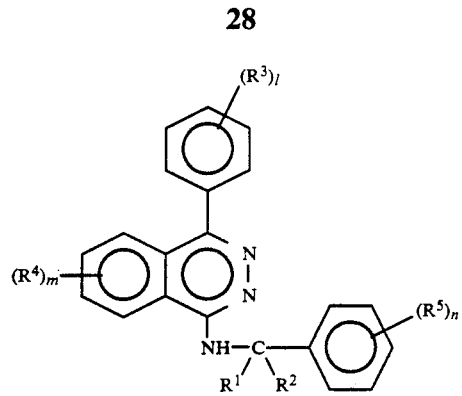

wherein $R^1$ is an alkyl or hydroxyalkyl group of 1-5 carbon atoms; $R^2$ is a hydrogen atom or an alkyl group of 1-5 carbon atoms; or $R^1$ and $R^2$, when taken together, may represent an alkylene group of 2-6 carbon atoms; $R^3$ and $R^4$ are independently a hydrogen or halogen atom, an alkyl or alkoxy group of 1-4 carbon atoms, or when two of $R^3$ are adjacently positioned, $(R^3)_l$ may represent a $-O-(CH_2)_p-O-$ group and/or when two of $R^4$ are adjacently positioned, $(R^4)_m$ may represent a $-O-(CH_2)_p-O-$ group; $R^5$ is a hydrogen or halogen atom, an alkyl or alkoxy group of 1-4 carbon atoms, a trifluoromethyl group or a hydroxy group, or when two of $R^5$ are adjacently positioned, $(R^5)_n$ may represent a $-O-(CH_2)_p-O-$ group; p is an integer of 1-3; l and m are independently an integer of 1-2; and n is an integer of 1-3, and optical isomers and pharmaceutically acceptable acid addition salts thereof.

2. The compounds according to claim 1 wherein $R^3$ and $R^4$ are independently a hydrogen or halogen atom, or an alkyl or alkoxy group of 1-4 carbon atoms.

3. The compounds according to claim 2 wherein $R^3$ and $R^4$ are independently a hydrogen, fluorine, or chlorine atom, or an alkyl or alkoxy group of 1-3 carbon atoms.

4. The compounds according to claim 3 wherein l and m are an integer of 1.

5. The compounds according to claim 4 wherein $R^3$ and $R^4$ are independently a hydrogen or chlorine atom, or an alkyl group of 1-3 carbon atoms.

6. The compounds according to claim 5 wherein $R^3$ is a hydrogen or chlorine atom or an alkyl group of 1-3 carbon atoms; and $R^4$ is a hydrogen atom.

7. The compounds according to claim 6 wherein $R^1$ is an alkyl group of 1-5 carbon atoms or a hydroxyalkyl group of 1-3 carbon atoms; $R^2$ is a hydrogen atom or an alkyl group of 1-5 carbon atoms; or $R^1$ and $R^2$, taken together, represent an alkylene group of 4-6 carbon atoms.

8. The compounds according to claim 7 wherein $R^1$ is an alkyl group of 1-5 carbon atoms; $R^2$ is a hydrogen atom or an alkyl group of 1-5 carbon atoms; or $R^1$ and $R^2$, taken together, represent an alkylene group of 4-6 carbon atoms.

9. The compounds according to claim 8 wherein $R^5$ is a hydrogen or halogen atom, an alkyl or alkoxy group of 1-4 carbon atoms, or a trifluoromethyl group; or when two of $R^5$ are adjacently positioned, $(R^5)_n$ may represent a $-O-(CH_2)_p-O-$ group.

10. The compounds according to claim 9 wherein $R^5$ is a hydrogen or halogen atom, or an alkyl or alkoxy group of 1-4 carbon atoms.

11. The compounds according to claim 10 wherein n is an integer of 1.

12. A pharmaceutical composition which comprises one of the compounds according to claim 1 together with a pharmaceutically acceptable carrier therefor.

13. A pharmaceutical composition according to claim 12 which is useful as a platelet aggregation inhibitory agent containing an effective platelet aggregation inhibitory amount of the compound(s) of claim 1.

* * * * *